United States Patent
Grey

(10) Patent No.: US 6,310,224 B1
(45) Date of Patent: Oct. 30, 2001

(54) EPOXIDATION CATALYST AND PROCESS

(75) Inventor: Roger A. Grey, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/765,812

(22) Filed: Jan. 19, 2001

(51) Int. Cl.$^7$ .................. C07D 301/03; C07D 301/06
(52) U.S. Cl. ................ 549/523; 549/532; 549/533
(58) Field of Search ................ 549/523, 532, 549/533

(56) References Cited

U.S. PATENT DOCUMENTS

| | | | |
|---|---|---|---|
| 5,646,314 | 7/1997 | Crocco et al. | 549/531 |
| 5,744,619 | 4/1998 | Nemeth et al. | 549/523 |
| 5,780,654 | 7/1998 | Nemeth et al. | 549/531 |
| 6,005,123 | 12/1999 | Dessau et al. | 549/531 |
| 6,008,388 | 12/1999 | Dessau et al. | 549/531 |
| 6,063,942 | 5/2000 | Grey | 549/523 |

FOREIGN PATENT DOCUMENTS

| | | |
|---|---|---|
| 1001038 | 6/1989 | (BE) . |
| 19600709 | 7/1997 | (DE) . |
| 4-352771 | 12/1992 | (JP) . |
| H8-269029 | 10/1996 | (JP) . |
| H8-269030 | 10/1996 | (JP) . |
| WO 96/02323 | 2/1996 | (WO) . |
| WO 97/31711 | 4/1997 | (WO) . |
| WO 97/25143 | 7/1997 | (WO) . |
| WO 97/47386 | 12/1997 | (WO) . |

OTHER PUBLICATIONS

Synthesis of Propylene Oxide from Propylene, Oxygen, and Hydrogen Catalyzed by Palladium–Platinum–Containing Titanium silicalite By: R. Meiers et al (1998).

*Primary Examiner*—Ba K. Trinh
(74) *Attorney, Agent, or Firm*—William C. Long

(57) ABSTRACT

In a process for the production of an oxirane compound by reaction of olefins, oxygen and hydrogen using a noble metal on titanium or vanadium silicalite catalyst the improvement wherein the catalyst is doped with a substantially non-reduced metal dopand.

5 Claims, No Drawings

EPOXIDATION CATALYST AND PROCESS

RELATED APPLICATIONS

The present application is related to U.S. Pat. No. 6,063,942 issued May 16, 2000 to the same inventor.

FIELD OF THE INVENTION

This invention relates to the epoxidation of olefins such as propylene by reaction of the olefin with hydrogen and oxygen using a metal doped noble metal on titanium silicalite catalyst, an essential feature of the invention being that reduction of the dopand is substantially avoided prior to use. In accordance with the invention the undesirable hydrogenation of the olefin during the epoxidation reaction is substantially avoided.

BACKGROUND OF THE INVENTION

It is known to epoxidze olefins such as propylene to form propylene oxide by reaction of propylene, hydrogen and oxygen using a catalyst comprised of palladium and platinum or titanium silicalite. See "Synthesis of Propylene Oxide from Propylene, Oxygen, and Hydrogen Catalyzed by Palladium-Platinum-Containing Titanium Silicalite" By: R. Meiers, U. Dingerdissen, and W. F. Holderich, Journal of Catalysis 176, 376–386 (1998). A feature of such prior procedures has been the reduction of the catalysts prior to use in the epoxidation reaction. The prior systems have been characterized by the undesirable formation of excessive amounts of propane which results from hydrogenation of the propylene reactant.

SUMMARY OF THE INVENTION

In accordance with the present invention, it has been found that olefin hydrogenation during the epoxidation is reduced to a remarkable extent where the metal doped noble metal catalyst, eg Pd/Pt on titanium silicalite, is not completely reduced either by chemical or thermal means prior to use in the epoxidation reaction.

DETAILED DESCRIPTION OF THE INVENTION

The catalyst used in accordance with this invention comprises palladium incorporated with titanium containing zeolite, which can be prepared in accordance with known procedures. As a critical feature, the catalyst also comprises a metal doping component which is in substantially non-reduced state. Suitably at least 10% and preferably 50–100% of the doping component has a valence above zero, illustratively a valence of plus 2 in the case of platinum.

The preferred doping component is platinum although other components including silver, copper, gold and the like are useful. The doping component can be used in catalytic amounts relative to palladium, eg. a weight ratio of metal dopand to palladium of as low as 1:40 can be used, preferably the ratio is 1:30–1:1.

The preparation procedure of U.S. Pat. No. 6,063,942 is conveniently used wherein ion exchange preparation is employed and the resulting catalyst without drying or calcining is used in the epoxidation. By such a procedure reduction of the doping component is essentially avoided.

Also the doped catalyst can be isolated and dried at mild conditions and subsequently used for the epoxidation reaction.

Sequential preparation procedures wherein the catalyst components are separately incorporated with the silicalite with or without drying between stages provided substantial reduction of the dopand metal is avoided.

The catalysts to be prepared and used in the present invention are comprised of a titanium or vanadium zeolite and a noble metal (preferably an element of Group VIII of the Periodic Table). Suitable zeolites are those crystalline materials having a porous molecular sieve structure with titanium or vanadium atoms substituted in the framework. The choice of zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1- butene. Where the olefin is propylene, the use of a TS-1 titanium silicalite or vanadium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are well known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian U.S. Pat. No. 1,001,038). Also suitable for use are the titanium-containing molecular sieves having framework structures, isomorphous to zeolite beta, mordenite, ZSM-48, ZSM-12 and MCM41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2(1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 20 weight percent, preferably 0.1 to 5 weight percent.

In accordance with the invention, the zeolite in particulate form is slurried in a suitable solvent such as water or methanol or mixtures, and both the noble metal and metal dopand are incorporated into the zeolite by contact with a solution containing a soluble compound of the metals, for example, aqueous Pd tetraammine chloride and Pt tetraammine chloride with or without added ammonium hydroxide. There are no particular restrictions other then solubility regarding the choice of metal compound or complex used as the source of the noble metal. For example, suitable compounds for such purpose include the nitrates, sulfates, halides (e.g., chlorides, bromides), carboxylates (e.g. acetate), and amine complexes of noble metals and dopand metals.

Ambient temperatures are suitable for the catalyst preparation although higher or lower temperatures, eg. 0°–200° C., can be used. Generally the catalyst preparation is complete in an hour or so although longer or shorter times, eg. 5 minutes—24 hours can be used.

As a special feature of the invention, the slurry resulting from the catalyst preparation comprised of the metals in non-reduced form can be used directly for olefin epoxidation. For example, after completion of the catalyst preparation the temperature can be adjusted to the desired epoxidation temperature and oxygen, hydrogen and olefin reacted directly in the catalyst containing slurry to form epoxide. Epoxidation results achieved thereby can be better than those achieved by prior procedures where catalyst is dried and calcined before use. The effect is also achieved where the catalyst is isolated before use provided substantial reduction is avoided.

While it is preferred to prepare fresh catalyst and use the catalyst directly in the epoxidation reaction, benefits can be achieved by adding a noble metal and dopand ion exchangeable complex to a slurry which contains deactivated catalyst prepared by conventional procedures or by the procedures described above.

The olefin to be epoxidized can be any organic compound containing at least one site of ethylene unsaturation (i.e., at least one carbon-carbon double bond). The olefin can be aliphatic, aromatic or cycloaliphatic in character and may have either a linear or branched structure, with the site(s) of ethylenic unsaturation being terminal and/or internal. The olefin preferably contains 2–30 carbon atoms; the process of the invention is particularly suitable for epoxidizing $C_2$–$C_6$ mono-olefins. More than one double bond may be present as in a diene or triene for example. The olefin may be a hydrocarbon (i.e., contain only carbon and hydrogen atoms) or may contain functional groups such as halide, carboxyl, hydroxyl, ether, carbonyl, cyano, or nitro, groups or the like.

Typical examples of suitable olefins include ethylene, propylene, 1-butene, cis- and trans-2-butene, isobutene, 1,3-butadiene, pentenes, isoprene, hexenes, octenes, nonenes, decenes, undecenes, dodecenes, cyclopentene, cyclohexene, dicyclopentadiene, vinylcylohexane, vinyl cyclohexene, allylchloride, allyl alcohol, methallyl chloride, methallyl alcohol, alkyl acrylates and methacrylates, unsaturated fatty acids and esters thereof, styrene, alpha-methylstyrene, divinylbenzene, indene and stilbene. Mixtures of olefins may, of course, be utilized if so desired. The process of this invention is especially useful for converting propylene to propylene oxide.

The process of the invention may be suitably conducted under the reaction conditions (e.g., temperature, pressure, reactant ratios) described in the following published patent applications: WO 96/02323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin feed ratio of from 0.00001 to 0.1.

The epoxidation is carried out in the liquid phase, and it is advantageous to work at a pressure of 1–100 bars. Suitable solvents used in catalyst preparation and in the epoxidation include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water. Methanol and methanol/water are preferred. Additional solvent can be added before or during epoxidation to improve process results.

Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2$=1:20 to 5:1 and is especially favorable at 1:5 to 2:1.

The molar ratio of oxygen to olefin is usually 1:1 to 1:20, and preferably 1:1.5 to 1:10. Relatively high O2 to olefin molar ratios (e.g., 1:1 to 1:3) may be advantageous for certain olefins. As the carrier gas, any desired inert gas can be used. The molar ratio of olefin to carrier gas is then usually in the range of 1:100 to 4:1, and especially 20:1 to 1:1.

As the inert carrier gas, noble gases such as helium, neon, argon, krypton and xenon are suitable in addition to nitrogen and carbon dioxide. Saturated hydrocarbons with 1–8, especially 1–6, and preferably with 1–4 carbon atoms, e.g., methane, ethane propane and n-butane, are also suitable. Nitrogen and saturated $C_1$–$C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

Modifiers such as are described in U.S. Pat. Nos. 6,008,388 and 6,005,123 can be used.

The following examples further illustrate the invention and comparative procedures.

EXAMPLE 1

Epoxidation with Tetraamminepalladium(II) Dibromide Added to TS1 (Comparative)

Tetraamminepalladium(II) dibromide (0.0186 grams) is dissolved in 20 grams of deionized water. This solution is added to a glass reactor equipped with a magnetic stir bar containing one gram of a titanium silicalite powder (TS1 with titanium=2.1 wt %), slurried in 87 grams of methanol. The mixture is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of methanol in the reactor during the run, the gases are bubbled through a glass vessel located before the reactor (also in the 45° C. bath) containing 250 grams of methanol. The vapor from the reactor is analyzed by on-line GC every hr. After termination of the experiment the liquid phase is analyzed by GC.

EXAMPLE 2

Epoxidation With Tetraamminepalladium(II) Dibromide and Tetraammineplatinum(II) Dichloride Added to TS1

A stock solution of tetraammineplatinum(II) dichloride is prepared by dissolving tetraammineplatinum(II) dichloride (0.0179 grams) in 20 grams of deionized water.

Tetraamminpalladium(II) dibromide (0.0186) grams is dissolved in 18 grams of deionized water. Two grams of the tetraammineplatinum(II) dichloride stock solution is added to the tetraamminepalladium(II) dibromide solution. The combined solution of the palladium and platinum salts is added to a glass reactor equipped with a magnetic stir bar containing one gram of a titanium silicalite powder (TS1 with titanium=2.1 wt %), slurried in 87 grams of methanol. The mixture is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of methanol in the reactor during the run, the gases are bubbled through a glass vessel located before the reactor (also in the 45° C. bath) containing 250 grams of methanol. The vapor from the reactor is analyzed by on-line GC every hr. After termination of the experiment the liquid phase is analyzed by GC.

EXAMPLE 3

Epoxidation with Isolated Tetraamminepalladium (II) Dibromide/TS1 (Comparative)

A glass reactor equipped with a magnetic stir bar containing one gram of tetraamminepalladium (II) dibromide impregnated TS-1 (prepared as in example 21) is slurried in a mixture of 87 grams of methanol and 20 grams of deionized water. The mixture is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of methanol in the reactor during the run, the gases are bubbled through a glass vessel located before the reactor (also in the 45° C. bath) containing 250 grams of methanol. The vapor from the reactor is analyzed by on-line GC every hr. After termination of the experiment the liquid phase is analyzed by GC.

EXAMPLE 4

Epoxidation with Isolated Tetraamminepalladium (II) Dibromide/TS1 and Tetraammineplatinum(II) Dichloride Added A stock solution of tetraammineplatinum(II) dichloride is prepared by dissolving tetraammineplatinum(II) dichloride (0.0179 grams) in 20 grams of deionized water.

Two grams of the stock solution is added to 18 grams of deionized water and this solution added to a glass reactor equipped with a magnetic stir bar containing one gram of a tetraamminepalladium(II) dibromide impregnated TS-1 (prepared as in example 21) slurried in 87 grams of methanol. The mixture is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume%), propylene (10 volume %), methane (0.5 volume %) and nitrogen (balance) is passed to bubble through the solution at a rate of 100 cc/minute at atmospheric pressure for the designated time. In order to keep a constant volume of methanol in the reactor during the run, the gases are bubbled through a glass vessel located before the reactor (also in the 45° C. bath) containing 250 grams of methanol. The vapor from the reactor is analyzed by on-line GC every hr. After termination of the experiment the liquid phase is analyzed by GC.

EXAMPLE 5

Epoxidation with Tetraamminepalladium Dichloride Added to TS1 (Comparative)

The reaction is conducted as in example 1, except that tetraamminepalladium(II) dichloride (0.014 grams) is used in place of tetraamminepalladium(II) dibromide.

EXAMPLE 6

Epoxidation with Tetraamminepalladium(II) Dichloride/TS1 and Tetraammineplatinum(II) Dichloride Added to TS1

The reaction is conducted as in example 2, except that tetraamminepalladium(II) dichloride (0.014 grams) is used in place of tetraamminepalladium(II) dibromide.

EXAMPLE 7

Epoxidation with Tetraamminepalladium(II) Dichloride/TS1 and Tetraammineplatinum(II) Dichloride Added to TS1

The reaction is conducted as in example 6, except that 4 grams of the stock solution of tetraammineplatinum(II) dichloride is used.

EXAMPLE 8

Epoxidation with Tetraamminepalladium(II) Dichloride/TS1 and Tetraammineplatinum(II) Dichloride Added to TS1

The reaction is conducted as in example 6, except that 1 gram of the stock solution of tetraammineplatinum(II) dichloride is used.

EXAMPLE 9

Epoxidation with Tetraamminepalladium(II) Dichloride/TS1 and Tetraammineplatinum(II) Dichloride Added to TS1

The reaction is conducted as in example 6, except that 0.5 gram of the stock solution of tetraammineplatinum(II) dichloride is used.

EXAMPLE 10

Epoxidation with Silver/TS1 and Added Tetraamminepalladium(II) Dichloride

Tetraamminepalladium(II) dichloride (0.0144 grams) is dissolved in 20 grams of deionized water. This solution is added to a glass reactor equipped with a magnetic stir bar containing one gram of Ag/TS1 (prepared as in example 22) slurried in 87 grams of methanol. The mixture is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of methanol in the reactor during the run, the gases are bubbled through a glass vessel before the reactor (also in the 45° C. bath) containing 250 grams of methanol. The vapor from the reactor is analyzed by on-line GC every hr. After termination of the experiment the liquid phase is analyzed by GC.

EXAMPLE 11

Epoxidation with Copper/TS1 and Added Tetraamminepalladium(II) Dichloride

The reaction is conducted as in example 10, except that Cu/TS1 (prepared as in example 23) is used instead of Ag/TS1.

EXAMPLE 12

Epoxidation with Gold/TS1 and Added Tetraamminepalladium(II) Dichloride

The reaction is conducted as in example 10, except that Au/TS1 (prepared as in example 24) is used instead of Ag/TS1.

EXAMPLE 13

Epoxidation with Tetraamminepalladium Dibromide Added to TS1 (Comparative)

The reaction is conducted as in example 1, except that the titanium silicalite contains 1.65 wt % titanium.

EXAMPLE 14

Epoxidation with Tetraamminepalladium(II) Dibromide and Tetraammineplatinum(II) Dichloride Added to TS1

The reaction is conducted as in example 2, except that the titanium silicalite contains 1.65 wt % titanium.

EXAMPLE 15

Epoxidation with Isolated Tetraamminepalladium (II) Dibromide and Tetraammineplatinum(II) Dichloride/TS1

The reaction is conducted as in example 3, except that the catalyst is prepared as in example 25.

EXAMPLE 16

Epoxidation with Isolated Tetraamminepalladium (II) Dibromide and Tetraammineplatinum(II) Dichloride/TS1 Pretreated with Nitrogen at 150° C.

The reaction is conducted as in example 3, except that the catalyst is prepared as in example 26.

EXAMPLE 17

Epoxidation with Impregnated Tetraamminepalladium(II) Dibromide/TS1 in Water Solvent (Comparative)

A glass reactor equipped with a magnetic stir bar containing one gram of a tetraamminepalladium(II) dibromide impregnated TS-1 (prepared as in example 21) slurried in 130 grams of deionized water is allowed to stir at 23° C. for 2 hrs. The glass reactor is then immersed in a constant temperature bath at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of water in the reactor during the run, the gases are bubbled through a glass vessel located before the reactor (also in the 45° C. bath) containing 250 grams of water. The vapor from the reactor is analyzed by on-line GC every hr. After termination of the experiment the liquid phase is analyzed by GC.

EXAMPLE 18

Atmospheric Epoxidation with Impregnated Tetraamminepalladium(II) Dibromide/TS1 and Added Tetraammineplatinum(II) Dichloride in Water Solvent A stock solution of tetraammineplatinum(II) dichloride is prepared by dissolving tetraammineplatinum(II) dichloride (0.0179 grams) in 20 grams of deionized water.

Add two grams of the stock solution containing tetraammineplatinum(II) dichloride to 18 grams of deionized water. Add this solution to a glass reactor equipped with a magnetic stir bar containing one gram of a tetraamminepalladium(II) dibromide impregnated TS-1 (prepared as in example 21) slurried in 110 grams of deionized water. The slurry is allowed to stir at 23° C. for 2 hrs. The glass reactor is then immersed in a constant temperature at 45° C. and the reactor equipped with a glass dip tube through which a mixture of oxygen (4 volume %), hydrogen (4 volume %), propylene (10 volume %), methane (0.5 volume %) and nitrogen (balance) is passed to bubble through the solution at a rate of 100 cc/minute at atmospheric pressure for the designated time. In order to keep a constant volume of water in the reactor during the run, the gases are bubbled through a glass vessel located before the reactor (also in the 45° C. bath) containing 250 grams of water. The vapor from the reactor is analyzed by on-line GC every hr. After termination of the experiment the liquid phase is analyzed by GC.

EXAMPLE 19

Epoxidation Under Pressure with Tetraamminepalladium(II) Dichloride Added to TS1 (Comparative)

Tetraamminepalladium(II) dichloride (0.014 grams) dissolved in 20 mL of methanol is added to a pressure reactor, equipped with a magnetic stir bar, containing 1 gram of titanium silicalite (TS1 with 2.1 wt % titanium) slurried in 100 mL of methanol. The slurry is stirred in air at 23° C. for 2 hr. The stir bar is removed and the pressure reactor assembled. The reactor is heated to 45° C. and the reactor pressurized to 200 psig by flowing a mixture of oxygen (4 volume %), hydrogen (4 volume %), propylene (6 volume %), methane (0.5 volume %) and nitrogen (balance) via dip tubes through the solution at a rate of 1380 cc/minute for the designated time. The reactor was stirred mechanically at 1600 rpm. In order to keep a constant volume of methanol in the reactor during the run, the gases are bubbled through a pressure vessel located before the reactor (also at 45° C.) containing 700 grams of methanol. The vapor from the reactor is analyzed by on-line GC every hr. After termination of the experiment the liquid phase is analyzed by GC.

EXAMPLE 20

Epoxidation Under Pressure with Tetraamminepalladium(II) Dichloride and Tetraammineplatinum(II) Dichloride Added to TS1

A stock solution of tetraammineplatinumII) dichloride is prepared by dissolving tetraammineplatinum(II) dichloride (0.0179 grams) in 20 grams of methanol.

Two mL of the stock solution of tetraammineplatinum(II) dichloride is added to 18 mL of a methanol solution of tetraamminepalladium(II) dichloride (0.014 grams). The combined solution is added to a pressure reactor, equipped with a magnetic stir bar, containing 1 gram of titanium silicalite (TS1 with 2.1 wt % titanium) slurried in 100 mL of methanol. The slurry is stirred in air at 23° C. for 2 hrs. The stir bar is removed and the pressure reactor assembled. The reactor is heated to 45° C. and the reactor pressurized to 200 psig by flowing a mixture of oxygen (4 volume %), hydrogen (4 volume %), propylene (6 volume %), methane (0.5 volume %) and nitrogen (balance) via dip tubes though the solution at a rate of 1380 cc/minute for the designated time. The reactor was stirred mechanically at 1600 rpm. In order to keep a constant volume of methanol in the reactor during the run, the gases are bubbled through a pressure vessel located before the reactor (also at 45° C.) containing 700 grams of methanol. The vapor from the reactor is analyzed by on-line GC every hr. After termination of the experiment the liquid phase is analyzed by GC.

EXAMPLE 21

Preparation of Tetraamminepalladium(II) Dibromide Impregnated TS-1 (Comparative)

Tetraamminepalladium(II) dibromide (0.48 gram) is dissolved in 40 grams of deionized water. This solution is added with stirring over a 10 minute period to a slurry containing 30 grams of titanium silicalite powder (TS1 with 2.1 wt % titanium) in 80 grams of deionized water. The combined slurry is allowed to stir at 23° C. for 2 hrs. The solvent is removed by rotoevaporation by maintaining the bath temperature at 55° C. The solids are dried in a vacuum oven (1 torr) at 50° C. for 4 hrs. The dried solids (28.6 grams) analyzed for 0.37 wt % palladium, 2.06 wt % titanium, 0.55 wt % bromide and 0.12 wt % nitrogen.

EXAMPLE 22

Preparation of Silver/TS1 by Ion Exchange

Silver hexafluorophosphate (0.48 gram) is dissolved in 10 grams of deionized water. This solution is added with stirring over a 5 minute period to a slurry containing 20 grams of a titanium silicalite (TS1 with 2.1 wt% titanium) in 80 grams of deionized water. The slurry is allowed to stir at 23° C. for 2 hrs. The solvent is removed by rotoevaporation by maintaining the bath temperature at 55° C. The solids are dried in a vacuum oven (1 torr) at 50° C. for 4 hrs. The dried solids (19 grams) analyzed for 0.15 wt % silver and 2.19 wt % titanium.

EXAMPLE 23

Preparation of Copper/TS1 by Ion Exchange

Tetraamminecopper (II) dichloride (0.42 gram) is dissolved in 10 grams of deionized water. This solution is added with stirring over a 5 minute period to a slurry containing 20 grams of titanium silicalite powder (TS1 with 2.1 wt % titanium) in 80 grams of deionized water. The slurry is allowed to stir at 23° C. for 1 hr. The solids are separated from the solution by centrifuge. The solids are slurried with deionized water (100 grams) and centrifuged five more times. The solids are dried in a vacuum oven (1 torr) at 50° C. for 4 hrs. The dried solids (19 grams) analyzed for 0.033 wt % copper, 2.0 wt % titanium, 0.1 wt % nitrogen and less than 10 ppm chlorine.

EXAMPLE 24

Preparation of Gold/TS1 by Glycol Treatment

A beaker equipped with a magnetic stir bar is charged with gold oxide powder (60mg). To this, 10 grams of ethylene glycol is added and the mixture stirred at 23° C. for 3 hrs to give a purple/maroon solution. Add this solution drop wise over a 5 minute period to 10 grams of titanium silicalite (TS1 with 1.65 wt % titanium) slurried in 50 grams of water. The slurry is stirred at 23° C. for 24 hrs. The solids are separated by centrifuge. The solids are slurried with deionized water (80 grams) and centrifuged four more times. The solids are dried in a vacuum oven (1 torr) at 50° C. for 4 hrs. The solids (9.5 grams) analyzed for 0.15 wt % gold and 1.4 wt % titanium.

EXAMPLE 25

Preparation of Tetraamminepalladium(II) Dibromide and Tetraammineplatinum(II) Dichloride Impregnated TS-1

Tetraamminepalladium(II) dibromide (0.34 gram) and Tetraammineplatinum(II) dichloride (0.036 gram) is dissolved in 160 grams of deionized water. This solution is added with stirring over a 10 minute period to a slurry containing 20 grams of titanium silicalite powder (TS1 with 1.65 wt % titanium) in 50 grams of deionized water. The combined slurry is allowed to stir at 23° C. for 2 hrs. The solvent is removed by rotoevaporation by maintaining the bath temperature at 55° C. The solids are dried in a vacuum oven (1 torr) at 50° C. for 4 hrs. The dried solids (19 grams) analyzed for 0.4 wt % palladium, 0.09 wt % platinum 1.65 wt % titanium, 0.5 wt % bromide, and 0.12 wt % nitrogen.

EXAMPLE 26

Nitrogen Pretreatment of Tetraamminepalladium(II) Dibromide and Tetraammineplatinum(II) Dichloride Impregnated TS-1

Tetraamminepalladium(II) dibromide and Tetraammineplatinum(II) dichloride impregnated TS-1 (5 grams) as prepared in example 25, is placed in a quartz tube. The tube is placed in a tube furnace and purged with nitrogen at 100 cc/minute. The tube is heated at 150° C. for 22 hrs and then cooled to 23° C. The solids (4.85 grams) analyzed for 0.42 wt % palladium, 0.07 wt % platinum, bromide =0.3 wt %, chloride=100 ppm, nitrogen=0.13 wt %.

Results obtained from the above examples are presented in the following Table 1.

TABLE 1

| Ex. # | Catalyst | Metal Additive | Vol % PO | Vol % Propane | ° C. | ATM | Hrs | Solvent |
|---|---|---|---|---|---|---|---|---|
| 1 | Pd(NH4)4Br/TS1 Insitu | None | 0.28 | 0.18 | 45 | 1 | 66 | MeOH/H2O |
| 2 | Pd(NH4)4Br2/TS1 Insitu | Pt(NH3)4C12 | 0.29 | 0.02 | 45 | 1 | 46 | MeOH/H2O |
| 3 | Pd(NH4)4Br2/TS1 Isolate | None | 0.31 | 0.26 | 45 | 1 | 42 | MeOH/H2O |
| 4 | Pd(NH4)4Br2/TS1 Isolate | Pt(NH3)4C12 | 0.2 | 0.01 | 45 | 1 | 46 | MeOH/H2O |
| 5 | Pd(NH4)4C12/TS1 Insitu | None | 0.33 | 0.2 | 45 | 1 | 40 | MeOH/H2O |
| 6 | Pd(NH4)4C12/TS1 Insitu | Pt(NH3)4C12 | 0.31 | 0.02 | 45 | 1 | 68 | MeOH/H2O |
| 7 | Pd(NH4)4C12/TS1 Insitu | Pt(NH3)4C12 0.2 wt % Pt | 0.32 | 0.02 | 45 | 1 | 46 | MeOH/H2O |
| 8 | Pd(NH4)4C12/TS1 Insitu | Pt(NH3)4C12 0.05 wt % Pt | 0.3 | 0.04 | 45 | 1 | 68 | MeOH/H2O |
| 9 | Pd(NH4)4C12TS1 Insitu | Pt(NH3)4C12 0.025 wt % Pt | 0.3 | 0.1 | 45 | 1 | 40 | MeOH/H2O |
| 10 | 0.15 wt % Ag/TS1 isolate | Pd(NH4)4C12 | 0.2 | 0.01 | 45 | 1 | 45 | MeOH/H2O |
| 11 | 0.033 wt % Cu/TS1 | Pd(NH4)4C12 | 0.2 | 0.02 | 45 | 1 | 64 | MeOH/H2O |
| 12 | 0.15 wt % Au/TS1 isolate | Pd(NH4)4C12 | 0.26 | 0.1 | 45 | 1 | 42 | MeOH/H2O |
| 13 | Pd(NH4)4Br2/TS1 Insitu Ti = 1.6 wt % | None | 0.3 | 0.17 | 45 | 1 | 40 | MeOH/H2O |
| 14 | Pd(NH4)4Br2/TS1 Insitu Ti = 1.6 wt % | Pt(NH3)4C12 | 0.32 | 0.04 | 45 | 1 | 90 | MeOH/H2O |
| 15 | Pd(NH4)4Br/TS1 Pt(NH3)4C12 Isolate Ti = 1.6 wt % | | 0.29 | 0.05 | 45 | 1 | 34 | MeOH/H2O |
| 16 | Pd(NH4)4Br2/TS1 Pt(NH3)4C12 Isolate Tl = 1.6 wt % 150C N2 pretreat | | 0.22 | 0.18 | 45 | 1 | 20 | MeOH/H2O |
| 17 | Pd(NH4)4Br/TS1 ISOLATE | None | 0.2 Peak | 0.03 | 60 | 1 | 42 | H2O |
| 18 | Pd(NH4)4Br2/TS1 ISOLATE | Pt(NH3)4C12 | 0.18 Peak | 0.015 | 60 | 1 | 20 | H2O |
| 19 | Pd(NH4)4C12/TS1 Insitu | None | 0.25 | 0.45 | 45 | 14 | 20 | MeOH |
| 20 | Pd(NH4)4C12/TS1 Insitu | Pt(NH3)4C12 | 0.15 | 0.15 | 45 | 14 | 20 | MeOH |

A comparison of Examples 1 and 2 demonstrates a major reduction in propane formation by practice of the invention. The comparison of Examples 3 and 4 demonstrates similar results as does a comparison of Examples 5 and 6. Examples 7–9 shows the effect of decreasing dopand amounts, a substantial effect being obtained even at very low dopand level (EXAMPLE 4).

Examples 10–12 illustrate the use of dopands other than platinum with palladium. A comparison of Examples 13 and 14 further demonstrates the improved results achieved through practice of the invention.

EXAMPLE 16 demonstrates the poor results achieved where the catalyst is reduced in nitrogen in accordance with the prior art.

A comparison of Examples 17 and 18 again demonstrate the advantages of practice of the invention as does a comparison of Examples 19 and 20.

From the above data it can be seen that the use of non-reduced metal doped noble metal on titanium silicate catalyst results in important process improvements in that olefin hydrogenation is significantly reduced.

I claim:

1. In a process for the epoxidation of an olefin by reaction of $O_2$, $H_2$, and olefin in contact with a noble metal containing titanium or vanadium silicalite, the improvement which comprises carrying out the reaction using a catalyst doped with a metal dopand which is substantially non-reduced.

2. In a process for the epoxidation of an olefin by reaction of $O_2$, $H_2$, and olefin in contact with a palladium containing titanium silicalite catalyst, the improvement which comprises carrying out the reaction using a catalyst doped with platinum, copper, silver or gold metal dopand, said dopand being substantially non-reduced.

3. The process of claim 2 wherein the metal dopand is a platinum dopand.

4. The process of claim 2 wherein the weight ratio of metal dopand to palladium is 1:30–1:1.

5. The process of claim 2 wherein the olefin is propylene.

* * * * *